US008382655B2

(12) United States Patent
Dela Cruz

(10) Patent No.: US 8,382,655 B2
(45) Date of Patent: Feb. 26, 2013

(54) ADJUSTABLE TOURNIQUET FOR VENOUS FLOW CONTROL

(75) Inventor: Ely N. Dela Cruz, Sunland, CA (US)

(73) Assignee: Ely N. Dela Cruz, Sun Valley, CA (US)

( * ) Notice: Subject to any disclaimer, the term of this patent is extended or adjusted under 35 U.S.C. 154(b) by 256 days.

(21) Appl. No.: 12/925,612

(22) Filed: Oct. 26, 2010

(65) Prior Publication Data

US 2012/0101329 A1    Apr. 26, 2012

(51) Int. Cl.
*A61F 5/00* (2006.01)
(52) U.S. Cl. .................................................. 600/38
(58) Field of Classification Search ............. 600/38–41; 128/897–898
See application file for complete search history.

(56) References Cited

U.S. PATENT DOCUMENTS

| | | | | |
|---|---|---|---|---|
| 3,999,653 A * | 12/1976 | Haigh et al. | ................... | 206/584 |
| 5,085,209 A * | 2/1992 | Gottschalk | ....................... | 600/41 |
| 5,645,404 A * | 7/1997 | Zelenak | ............................. | 417/1 |
| 5,855,548 A * | 1/1999 | Place | ................................ | 600/38 |
| 7,544,161 B1 * | 6/2009 | Wooten et al. | ................... | 600/38 |

* cited by examiner

Primary Examiner — Samuel Gilbert

(57) ABSTRACT

A disposable penile erection device that has a positive locking mechanism on the superficial veins around the base of a human penile organ. The device is a tubular structure adapted to the penis to be secured in loop configuration about the base of the penis to provide two (2) adjustable and lockable radial constriction force about the base of the penis. Methods for using the device are also provided.

2 Claims, 7 Drawing Sheets

LOCKED POSITION

LOCKED POSITION

UNLOCKED POSITION

LOCKED POSITION

UNLOCKED POSITION

ADJUSTABLE TOURNIQUET FOR VENOUS FLOW CONTROL

CROSS REFERENCE TO RELATED APPLICATION

None

FEDERALLY SPONSORED RESEARCH

Not Applicable

SEQUENCE LISTING

Not Applicable

BACKGROUND

1. Field

This application relates to adjustable tourniquet for venous flow control, specifically for treating erectile dysfunction.

2. Prior Art

Numerous treatments for impotence are known in the art, and include psychological therapies, hormonal therapy, administration of various vasodilators, surgery (e.g. vascular surgery or implantation of penile prosthesis). Vacuum devices and various external aids such as penile splints and constriction devices. More particularly U.S. Pat. No. 5,810,710 to Burgos describes constriction device composed of a pair of rigid C-shaped members hinged joined to form said split-ring. The disadvantage of this device is that it has to be applied prior to erection and is very difficult if not impossible to adjust once in place especially after erection has taken place. It is also rigid and could be uncomfortable and bothersome to one or both partners. U.S. Pat. No. 3,461,863 to Sullinger describes an adjustable constriction device consisting of a loop of flexible tubing having two apertures arranged at one end of the tubing which allow the other end to pass through and provide a means for fastening the device in place. Sullinger further describes the importance of the relative spacing of the two apertures and tube wall thickness to prevent or resist slippage of the device in response to the increased tension. The disadvantage of this device is that it could present a hygienic problem. U.S. Pat. No. 5,855,548 to Virgil A. describes a venous flow control device assisting in the maintenance of a penile erection or in preventing urinary incontinence. The device is a tubular structure adapted to be secured in a loop configuration about the penis to provide an adjustable radial constrictive force, about the base of the penis. One dis-advantage is it does not have a positive locking mechanism. The VFC device has a tendency to loosen during sexual intercourse especially a vigorous one. Another factor that could loosen the device is the presence of natural vaginal lubricant or personal lubricant applied to the penis and/or the vaginal area which could result in the slipping of the device resulting in loss of rigidity of the penis. The grasping means at both distal and proximal ends are formed by inserting annular or plastic rings. The insertion of annular bodies into the tubing does not provide a leak proof seal. Washing the unit with soap and water after each use can cause leakage into the tubing, which can be a source of contamination. Since the tubing material used in prior art is an opaque off-white colored latex and 'O' rings are used to seal the ends of the tubing, it is difficult to see the soapy solution seeping into the tubing. Therefore, any fluid, natural or otherwise can enter the tubing becoming an environment for bacteria to proliferate.

Although these devices, as well as other types of constriction or clamping devices known in the art, are capable of restricting blood flow from the penis, these devices are subject to several disadvantages in the treatment or prevention of erectile failure. One common disadvantage involves a lack of means to adjust tension and lock the device in place. It is important to restrict veinal outflow to maintain penile rigidity. Insufficient restriction prevent such devices to maintain an erection. Too much restriction may result in user discomfort, numbness and insensitivity which may result in damage to the penile tissue especially if left in place for an extended period of time. Some devices can not be adjusted without removing the clamping device resulting in loss of penile rigidity. Furthermore, since the degree of veinal restriction provided by prior devices depends in part on the stage of the individual's erection, a problem arises when such devices are adjusted to achieve tightness suitable for initial erection but subsequently becomes too restrictive thereafter.

SUMMARY

In accordance with one embodiment the adjustable tourniquet also referred to as 'ED Loop' with a locking device is more effective. It is designed to produce and maintain a voluntary and controlled penile erection by applying even, localized, and selected pressure circumferentially around the base of the penis.

One of the objectives is to provide a tourniquet which can be adjusted easily and quickly which will maintain its adjustment accurately. Other objectives are to provide a device which is simple in construction, not requiring any clamps and is compact and unobtrusive. A device that can be washed with soap and water before and after use without any fear of contamination and is inexpensive yet durable.

A single lock configuration can also be used.

Figure 7A:
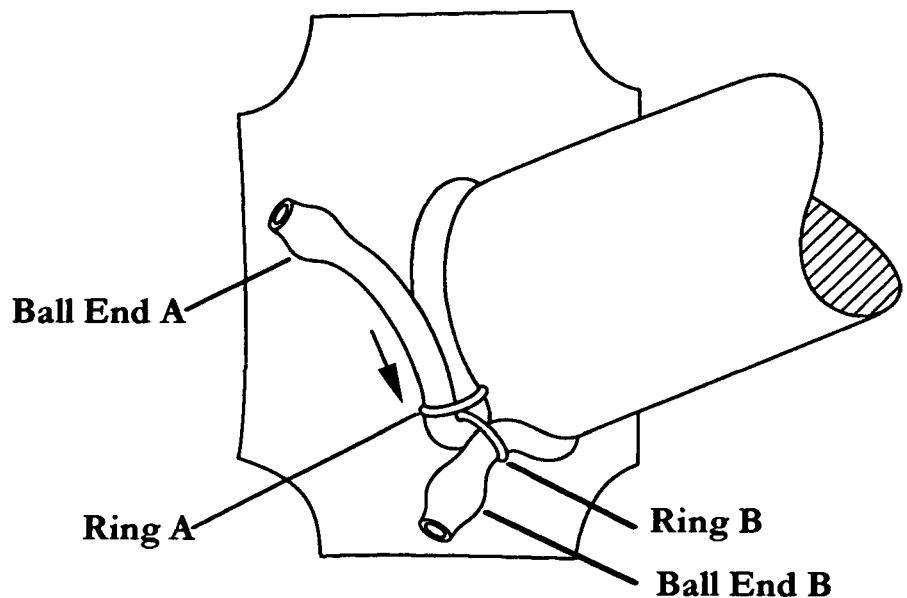

FIG. 7a shows the locked position of the single lock configuration when ring A is pushed towards ring B and ring B is pushed against ball end B.

Figure 7B:
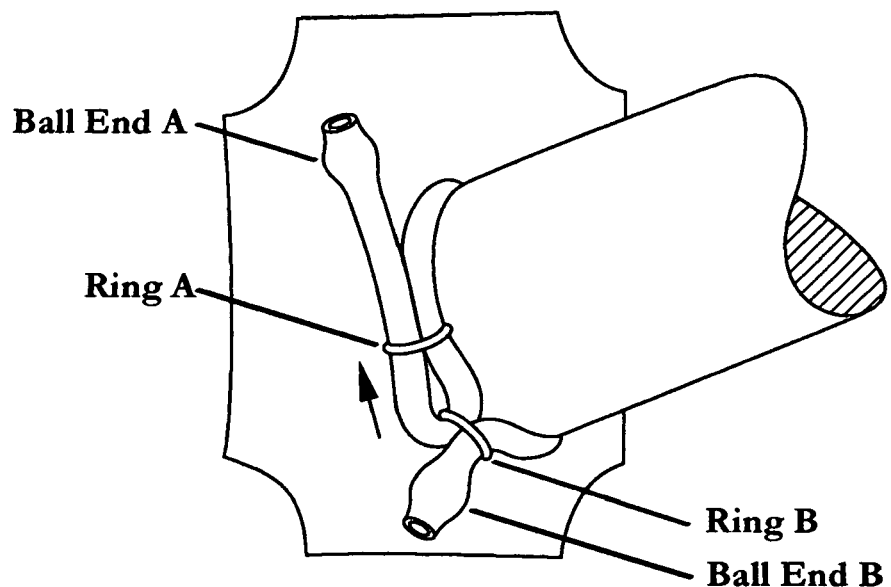

FIG. 7b shows the unlocked position when ring A is slid away from ring B.

DETAILED DESCRIPTION-FIRST EMBODIMENT

Figure 6A:
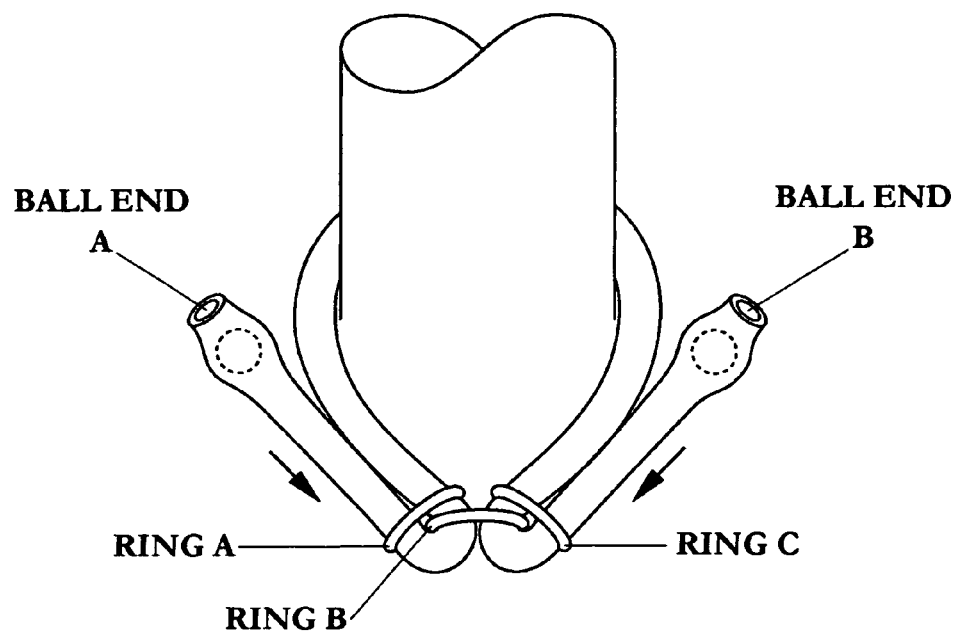
FIG. 6a shows the locked position of the multiple lock configuration when rings A and C are pushed against ring B.
Figure 6B:
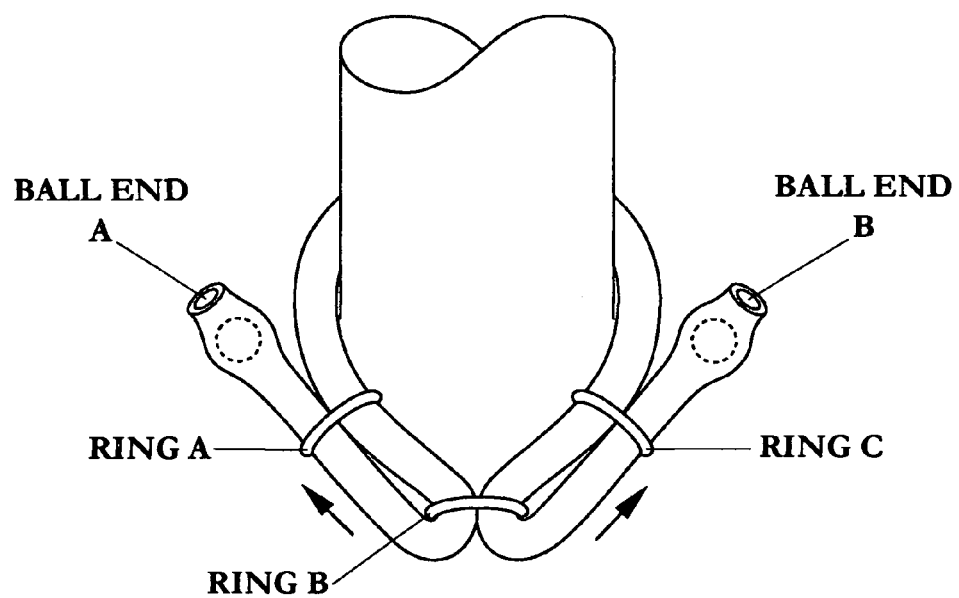
FIG. 6b shows the unlocked position when rings A and C are slid away from ring B.

Before describing the invention in detail, it is to be understood that the present invention is not limited to specific materials, configurations or particular methods of use, such as may vary. It is also to be understood the terminologies used for the purpose of describing particular embodiments only, and is not intended to be limiting. For example FIGS. 6a and 6b depict the on and off mechanism of the multiple lock device, while FIGS. 7a and 7b depicts the on and off mechanism of the Single lock device.

Figure 1:
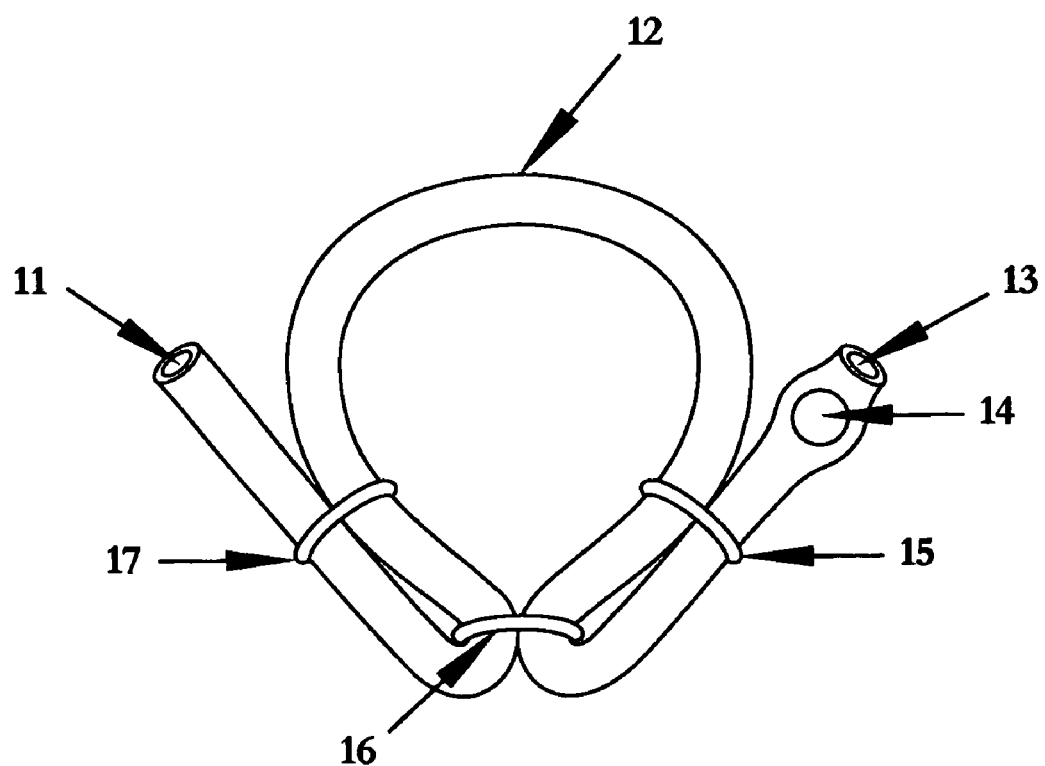
FIG. 1 is a perspective view of the tourniquet (ED Loop) of the present invention.
Figure 2:
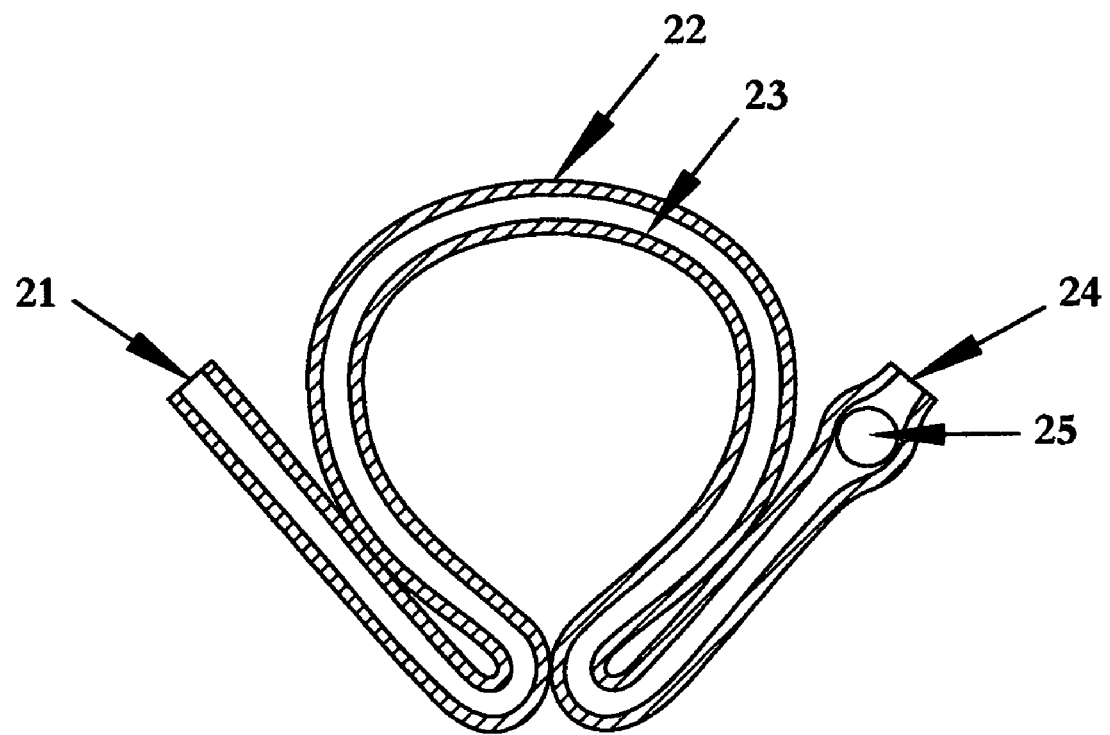
FIG. 2 is a cross section of the device showing the grasping means (a plastic ball) that doubles as a seal, keeping moisture out of the tubing eliminating a source of contamination.
Figure 3:
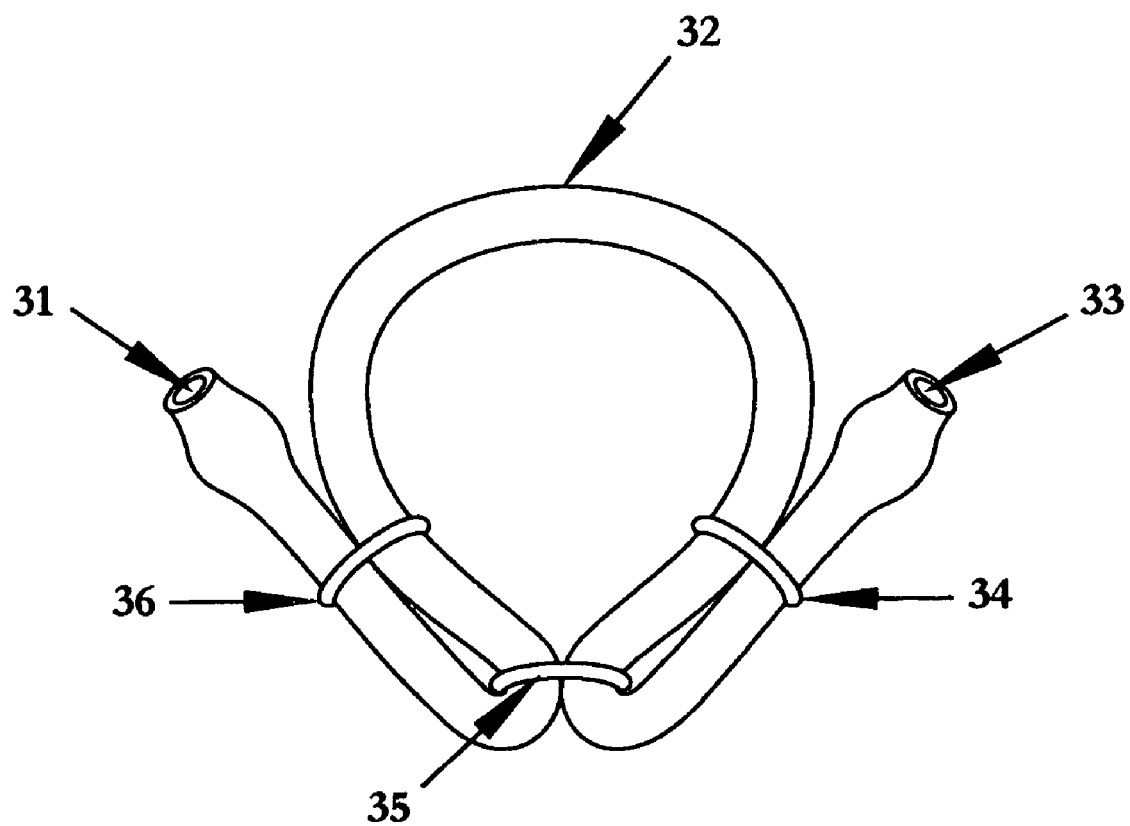

One embodiment relates to the ED Loop device as adapted for application to the penis. The device can not only be used to enhance and maintain a penile erection, but help in the treatment of incontinence as well. ED Loop can also take the place of the un-adjustable rings used in conjunction with Penile Pumps. Referring to FIG. 1, one embodiment of the device is that it is formed from a length of tubing having a central section #12 flanked by distal ends 11 and proximal end 13, the central section of the tubing has a substantially uniform diameter. The length of tubing may be selected to custom fit any individual user in either a pre-scrotal or post-scrotal position or to the size of an individual's penis.

Although only a small percentage of the population is sensitive to latex, the ED Loop is made of a combination of Silicone tubing, Polycarbonate rings and Polypropylene balls.

Other tubing materials which are useful include but are not limited to natural and synthetic elastomers such as methyl vinyl polysiloxane or the like, polyisobutylene, chloroprene polymers, polybutadiene, polyisoprene and natural rubber. Other materials will be readily apparent to those skilled in the art. The combination of tubing and a spherical ball is ideal in solving some problems that are present in the prior art. An enlarged segment of the tubing formed by a ball in the tubing is a more effective grasping means than one that is formed by an 'O' ring in the tubing. Since the tubing material used in prior art is an opaque color and an O-ring is used to seal the ends of the tubing, it would be difficult to see how the combination allows seepage of fluids into the tubing. A ball inserted at the end of the tubing as a grasping means forms a more effective seal in preventing liquid or fluid of any kind from entering the tubing.

Figure 4:
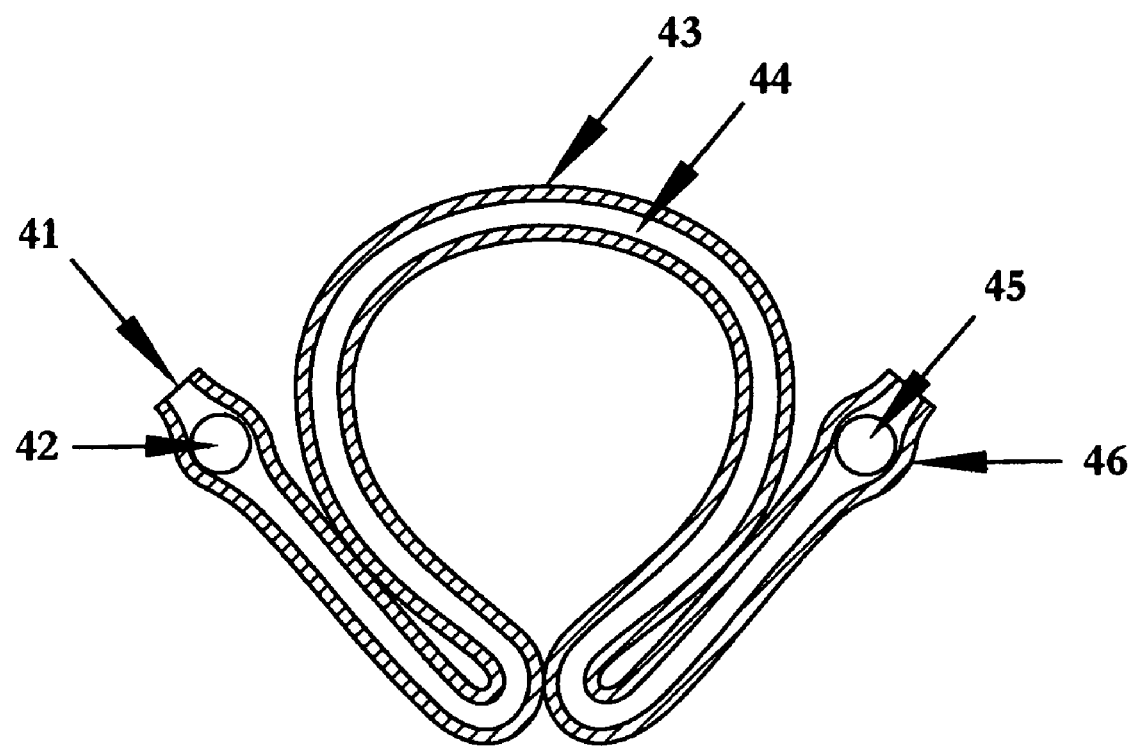
FIG. 4 is a cross-sectional view of FIG. 3 depicting optional finger grasping means disposed with in the tubing. These spherical objects also double as positive seals to keep moisture out of the device.

This can be proven by using a semi-transparent tubing and washing the two different ends with soap and water, one end sealed with an O-ring and the other sealed with a ball. You can see that the end sealed with a ball provides a more effective seal, thus eliminating the problem of contamination. Plastic balls 42 and 45 in FIG. 4 when inserted into distal end 41 and proximal end 46 form the said enlarged segment of tubing. The plastic balls are generally made of polypropylene but can also be substituted with nylon, acrylic, delrin or other suitable material.

OPERATION

Figure 5:
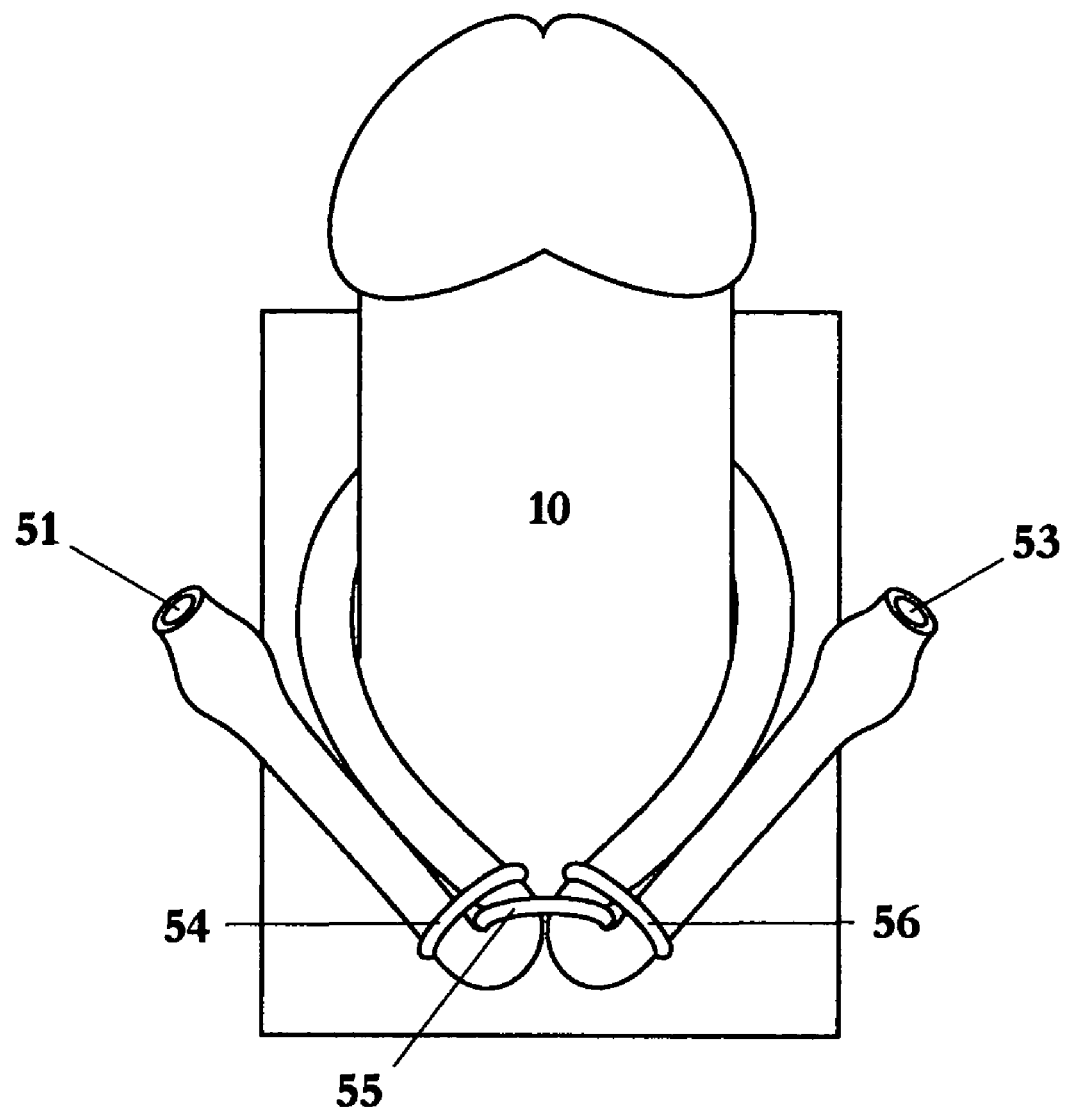
FIG. 5 is a pictorial representation of the ED Loop device in use.

In FIG. 5 the penis 10 is inserted through loop 52 (make sure the device is applied to the base of the penis). To tighten the device, one hand should hold ball end 51 and the other ball 53, both hands pulling outward. This action reduces the size of loop 52 to the desired tightness around the base of the penis. The device can then be locked into position by sliding rings 54 and 56 towards and against ring 55. Always remember to slide rings 54 and 56 toward and against ring 55 to lock the device. Rings 54, 55, and 56 are made of Polycarbonate material. Other substitute material can be polyoxymetylene, polypropylene or other suitable material.

CONCLUSION, RAMIFICATION AND SCOPE

Accordingly, the reader will see that consistent to one embodiment, the ED Loop is an effective device to maintain and enhance a penile erection. It has a more reliable locking mechanism which is easier to adjust and maintain it's form than prior art. Furthermore, with the use of spherical objects as seals, a more positive seal is created in both distal and proximal ends thus preventing any seepage into the tubing.

While the above description contains many specifications, these should not be construed as limitations on the scope of any embodiment, but as exemplification of the presently preferred embodiments thereof. Many other ramifications and variations are possible within the teachings of the various embodiments. For example, FIGS. 6A, 6B, 7A and 7B depicts the use of the locking mechanism in either a multiple or single lock configuration. Thus the scope of the invention should be determined by the appended claims and their Legal equivalents and not by the examples given.

The invention claimed is:

1. A device for application to a human penis and adapted to maintain a penile erection, comprising
    a length of tubing adapted to be applied to a human penis, having a central section, a first end and a second end, said first end and said second end each including a ball positioned within said tubing to seal said ends and provide grasping means,
    three annular rings A, B and C wherein said tubing is formed into a loop by passing said first end through said ring A then through said ring B then bending said tubing over said ring B and passing said first end back through said ring A and passing said second end through said ring C then through said ring B then bending said second end over said ring B and passing said second end back through said ring C,
    said rings A and C each having a locked position and an unlocked position wherein in said locked position said rings A and C are positioned against said ring B and in said unlocked positions said ring A is moved away from said ring B and positioned near said first end and said ring C is moved away from said ring B and positioned near said second end,
    constriction around the penis is achieved by increasing tension on said loop by pulling said first and second ends away from the penis when said loops A and C are in said unlocked position, tension is maintained by moving said loops A and C from said unlocked position to said locked position while pulling on said first and second ends, and tension is relieved by moving said rings A and C from said locked position to said unlocked position and pulling on said central section of said tubing on each side of the penis.

2. A device as set forth in claim 1 wherein said tubing is formed from latex rubber or silicone.

* * * * *